United States Patent [19]

Mack et al.

[11] 4,379,766

[45] Apr. 12, 1983

[54] SILYL ESTERS OF CARBOXYLIC ACIDS BY PHASE TRANSFER CATALYSTS

[75] Inventors: Mark P. Mack; Charles T. Berge, both of Ponca City, Okla.

[73] Assignee: Conoco Inc., Ponca City, Okla.

[21] Appl. No.: 383,388

[22] Filed: Jun. 1, 1982

[51] Int. Cl.³ .............................................. C07F 7/08
[52] U.S. Cl. ..................................... 260/413; 556/442
[58] Field of Search ......................... 556/442; 260/413

[56] References Cited

U.S. PATENT DOCUMENTS

| | | | |
|---|---|---|---|
| 2,573,302 | 10/1951 | Bidaub et al. | 556/442 |
| 3,542,831 | 11/1970 | Gowdy | 556/442 |
| 3,542,832 | 11/1970 | Roth | 556/442 |
| 4,028,391 | 6/1977 | Foley | 556/442 X |
| 4,176,131 | 11/1979 | Shih et al. | 556/442 |
| 4,329,484 | 5/1982 | Petersen | 556/442 |

*Primary Examiner*—Paul F. Shaver
*Attorney, Agent, or Firm*—Cortlan R. Schupbach, Jr.

[57] ABSTRACT

Silyl esters of carboxylic acids, of the general formula

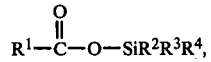

are formed under mild conditions in the presence of a phase transfer catalyst when a silicon halide is contacted with a carboxylic acid salt wherein $R^1$, $R^2$, $R^3$ and $R^4$ are each a hydrogen atom or a hydrocarbon radical. Suitable phase transfer catalysts include quaternary ammonium salts, cryptates and crown ethers.

9 Claims, No Drawings

SILYL ESTERS OF CARBOXYLIC ACIDS BY PHASE TRANSFER CATALYSTS

This invention relates to a manufacture of silyl esters of carboxylic acids. More specifically, this invention relates to the production of silyl esters of carboxylic acids under mild conditions in the presence of phase transfer catalysts by contacting a silicon halide with a carboxylic acid salt.

Silyl esters of carboxylic acids are generally known in the art. These materials are useful as coupling agents for glass fibers, crosslinking silicone rubber compositions, sequestering agents for hard water materials, water repellants for hydrophylic materials and in certain forms are useful for the retardation of water evaporation. Representative but non-exhaustive of the prior art representing such materials includes Chem Abstracts 81:90751v; U.S. Pat. No. 3,974,189, which shows the production of acyloxysilane compositions by reacting a chlorosilane with a carboxylic acid or carboxylic acid anhydride in the presence of an ion complexing agent; U.S. Pat. No. 2,573,302 which shows the production of methyl silyl acetates by reacting chlorosilane with anhydrous salts of acetic acid at room temperature, and Canadian Patent 488,531, which shows the production of such materials by reacting organic carboxylic salts with organosilicon halides. In addition, silyl esters synthesized as described in *Bulletin De L'Academie Polonaise Des Sciences*, Vol XXII No. 3, (1974), produced yields of only 50 to 80%. Such compounds are also prepared in the *Journal of the American Chemical Society*, 74, 2371 (1952). However, the yields are also low using this method.

In general, methods for making organosilicon halides are known. Alkyl silicon halides may be prepared by reacting alkyl magnesium halides with a silicon tetrahalide using an ether as a medium for the reaction. Alkoxy silicon halides are known to be prepared by reacting an alcohol with a polyhalosilicon compound.

However, these reactions are lengthy and are usually confined to a very specific set of reactants and products. It would be a great benefit to provide a method for generating silyl esters of carboxylic acids under mild anhydrous conditions with reagents that can be readily obtained commercially, thus greatly increasing the supply of these materials.

It is therefore an object of the present invention to provide a method for obtaining silyl esters of carboxylic acids. Other objects will become apparent to those skilled in this art as the description proceeds.

We have now discovered that silyl esters of carboxylic acids having the general formula

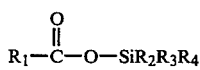

wherein $R_1$, $R_2$, $R_3$, and $R_4$ are, independently, hydrogen, cycloalkyl groups, aralkyl groups, alkaryl groups, aryl groups, and bicycloalkyl groups containing from 6 to 30 carbon atoms, and alkyl groups containing from 1 to 30 carbon atoms can be obtained by reacting a carboxylic acid salt with a silicon halide in the presence of a phase transfer catalyst.

The reaction is carried out under mild conditions at temperatures ranging from about 10° C. to about 150° C. Any pressure desired can be used which will maintain the starting materials as either liquid or solids and thus varies widely. However, normally temperatures of from about 10° C. to about 100° C. will be the most commonly used.

The reaction is carried out in the presence of phase transfer catalysts useful in promoting the reaction. Phase transfer catalysts are taught to be effective when in a system with two phases, the phase transfer agent in catalytic quantities brings one reactant from one phase into contact with a second reactant in a second phase such that the reaction between the two can occur at reasonable speed. Phase transfer catalysts are described in general in U.S. Pat. No. 3,992,432, which deals with quaternary salts as phase transfer catalysts.

In principle, the transfer of species may be carried out between any chemical phases, but normally organic phases will be used. The phase transfer agents useful in the present invention are highly lipophylic quaternary ammonium salts, cryptates, and crown ethers.

In general, carboxylic acid salts utilized in the practice of the present invention by using metal salts of the Group Ia metals of lithium, sodium, potassium, rubidium and cesium. Carboxylic acid salts of lithium, sodium, potassium, rubidium and cesium have the general formula

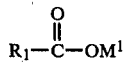

wherein $M^1$ represents lithium, sodium, potassium, rubidium and cesium and $R_1$ is as described above.

Group IIa metals have the general formula

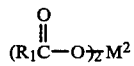

wherein $M^2$ is magnesium, calcium, strontium, barium and zinc and $R_1$ is as described above.

Many metals have multivalent states and carboxylic salts of metals of any state can be utilized. Normally, however, such materials will be found in their trivalent state with the general formula

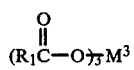

wherein $M^3$ is aluminum, titanium, vanadium, chromium or iron and $R_1$ is as described above.

The silicon halide utilized in the present invention has the general formula

wherein $R_2$, $R_3$, and $R_4$ can be cycloalkyl groups, aralkyl groups, alkaryl groups, aryl groups and bicycloalkyl groups, each containing from 6 to 30 carbon atoms, alkyl groups containing from 1 to 30 carbon atoms, hydrogen, —O—SiR$_3$, —OR,—NR$_2$, and wherein X is fluoride, chloride, bromide, or iodide, and wherein when any of $R_2$, $R_3$ or $R_4$ is halogen, said halogen is no more reactive than the X designated halogen.

Representative but non-exhaustive examples of the Group I carboxylic acid salts useful as starting materials in the practice of the present invention are
HCO$_2$Na
CH$_3$C$_6$H$_4$CO$_2$Li CH$_3$CO$_2$Cs
C$_6$H$_5$CO$_2$Cs
cyclo-C$_6$H$_{11}$CO$_2$Na
C$_6$H$_5$CH$_2$CO$_2$K
C$_{20}$H$_{41}$CO$_2$Rb
C$_6$H$_5$CO$_2$Na
CH$_3$CO$_2$Li
C$_4$H$_9$CO$_2$K
C$_{30}$H$_{61}$CO$_2$Rb
sodium bicyclo[2.2.2]octa-2-carboxylate
potassium bicyclo[2.2.1]hepta-2-carboxylate Representative but non-exhaustive examples of the Group II carboxylic acid salts are
(HCO$_2$)$_2$Ca
(CH$_3$CO$_2$)$_2$Ca
(iso-C$_3$H$_7$CO$_2$)$_2$Mg
(C$_2$H$_5$C$_6$H$_4$CO$_2$)$_2$ Sr
(sec-C$_4$H$_9$CO$_2$)$_2$Mg
(C$_6$H$_5$C$_2$H$_4$CO$_2$)$_2$Ba
(CH$_3$CO$_2$) (C$_6$H$_5$CO$_2$)Zn
magnesium bis-bicyclo[3.2.1]octa-2-carboxylate
(C$_{25}$H$_{51}$CO$_2$)$_2$Sr
(cyclo-C$_8$H$_{15}$CO$_2$)$_2$Ba Representative but non-exhaustive examples of the carboxylic acid metal salts are
(HCO$_2$)$_3$Al
(C$_2$H$_5$CO$_2$)$_3$Ti
(C$_6$H$_5$CO$_2$) (C$_6$H$_5$CH$_2$CO$_2$)$_2$V
(CH$_3$CO$_2$)$_2$(C$_{17}$H$_{35}$CO$_2$)Cr
(n-C$_3$H$_7$CO$_2$)$_3$Fe
(cyclo-C$_6$H$_9$CO$_2$)$_2$(C$_2$H$_5$CO$_2$)Al
(C$_6$H$_5$CO$_2$)$_2$(CH$_3$CO$_2$)Cr
(CH$_3$CO$_2$)$_3$Fe

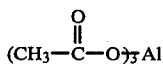

$$(CH_3-\overset{\overset{\displaystyle O}{\|}}{C}-O)_3 Al$$

Representative but non-exhaustive examples of the silicon halides useful in the practice of the present invention are
(CH$_3$)$_3$SiCl
(CH$_3$)$_3$SiBr
(C$_6$H$_5$) (CH$_3$)$_2$SiCl
(CH$_3$)$_2$SiClBr
(C$_7$H$_{15}$) (CH$_3$)SiFBr
(C$_2$H$_5$) (C$_6$H$_5$C$_2$H$_4$)SiFCl
(CH$_3$C$_6$H$_4$)$_2$(CH$_3$)SiI
(C$_6$H$_5$C$_2$H$_2$) (CH$_3$)$_2$SiCl
(C$_6$H$_5$CH$_4$) (CH$_3$) (C$_2$H$_3$)SiBr
(C$_2$H$_5$) (CH$_3$) (cyclo-C$_6$H$_{11}$)SiCl
(iso-C$_3$H$_7$) (CH$_3$) (C$_6$H$_5$)SiBr
(cyclo-C$_6$H$_{11}$) (C$_3$H$_7$) (CH$_3$)SiI
(C$_{20}$H$_{41}$) (CH$_3$) (iso-C$_3$H$_7$)SiI
(bicyclo[2.2.2]octa-1-ane) (C$_2$H$_5$) (sec-C$_4$H$_9$)SiCl Phase transfer catalysts useful in the practice of the present invention are those generally effective with the particular materials used. Phase transfer catalysts used can be of the quaternary ammonium salts, crown ethers, and cryptates.

Quaternary ammonium salts phase transfer catalysts useful in the present invention are generally described in U.S. Pat. No. 3,992,432. Representative but non-exhaustive examples of such effective phase transfer catalysts are hexadecyltrihexylammonium bromide; trioctylethylammonium bromide; tridecylmethylammonium chloride; didodecyldimethylammonium chloride; tetraheptylammonium iodide; dioctadecyldimethyl ammonium chloride; tridecylbenzylammonium chloride; ditricosylmethylammonium chloride; tricaprylyldodecylammonium p-toluene sulfonate; tetranonylammonium hydroxide; N,N,N,N-tetramethyl-N,N-ditetradecyl-p-xylene-α,α'-diammonia dichloride; N,N,N'N'-tetramethyl-N,N'-dioctadecyl-x-dodecyl-y-xyleneα,α'diammonium dichloride; N,N-dioctadecyl-N-methylN-(sodiocarboxylmethyl)-ammonium chloride; N,N,N'-N-tetramethyl-N,N'-dioctadecyl-p-xyleneα,α'-diammonium dichloride; N,N,N',N'-tetramethyl-N,N'dioctadecyl-1,2-ethyl diammonium dibromide; N,N'-dimethyl-N,N,N',N'-tetraheptadecyl-2-butene-1,4-diammonium chloride, tetra-n-butylammonium bromide or mixtures of these.

Both crown ether and cyptate phase transfer catalysts are likewise useful in the practice of the present invention. Macrocyclic (crown ether) catalysts and macrobicyclic (cryptate phase transfer catalysts) are useful. Normally these materials are extremely complex and have no encompassing general formulas. These materials are chosen based upon the particular metal or metals used. For optimum reaction, mixtures of carboxylic metal salts will require a mixture of crown ether or cryptate phase transfer catalysts. For example 12-crown-4 is optimal for lithium, 15-crown-5 is optimal for sodium, and 18-crown-6 is optimal for potassium. Representative but non-exhaustive examples of such materials useful in the practice of the present invention include 15-crown-5; 18-crown-6; dibenzo-18-crown-6; dicyclohexyl-18-crown-6; benzo-15-crown-5; alkyl-18-crown-6; alkyl-2,2,2-cryptate benzo-2,2,2-cryptate; 2,2,2-cryptate; 2,2,1-cryptate; 2,1,1-cryptate; dibenzo-24-crown-6; 12-crown-4 and mixtures of these.

Phase transfer catalysts are normally present in the reaction of concentrations of from about 0.001% by weight to about 10% by weight based upon the weight of reactants present. From about 0.01 to about 5.0% by weight is preferred.

Normally the reaction of the present invention will be carried out in the presence of an inert solvent. Any solvent inert with respect to the reaction can be used, but preferred solvents are alkanes such as hexanes, heptanes and isooctanes and the like; aromatics such as benzene, toluene; and mixed hydrocarbon solvents such as low polynuclear aromatic solvents, and raffinate solvents. Mixtures of these inert solvents can be used.

The invention is more concretely described with reference to the examples below wherein all parts and percentages and by weight unless otherwise specified. The examples are provided to illustrate the present invention and not to limit it.

EXAMPLE 1

A 250 milliliter (ml) flask was charged with sodium benzoate (2.0472 grams, 0.0142 moles), butylmethyl phenylchlorosilane (2.64 grams, 0.0124 moles), 200 ml dry tetrahydrofuran, and 0.01 grams of 18-crown-6. The flask was purged with argon and allowed to stir at room temperature (approximately 22° C.) for three hours. The reaction product was filtered and the supernate showed a single carbonyl band at 1705 centimeters$^{-1}$ in the infrared region indicating the presence of a silyl ester bond.

EXAMPLE 2

A 500 ml round bottom flask was thoroughly dried, purged with argon and charged with sodium benzoate (6.79 grams, 0.471 moles), t-butyldimethylchlorosilane (7.11 grams, 0.0471 moles), approximately 200 ml of dry, oxygenfree hexane, and 0.03 grams of 18-crown-6. The reaction was stirred under argon at room temperature (approximately 22° C.) for one hour. A sample was analyzed by infrared spectrometry and showed the presence of a single carbonyl band at 1710 cm$^{-1}$.

EXAMPLE 3

A 30 ml flask was charged with sodium benzoate (0.21 grams, 0.00146 moles), t-butyldimethylchlorosilane (0.22 grams, 0.00146 moles), and approximately 20 ml of dry, oxygen-free hexane. The reaction was allowed to stir at room temperature (approximately 22° C.) for one hour. A sample was withdrawn and analyzed by infrared spectroscopy. There was substantially no reaction as evidenced by the absence of a strong carbonyl band at approximately 1700 centimeters$^{-1}$.

The reaction mixture was then catalyzed with 0.01 grams of 18-crown-6 and the reaction allowed to stir for 1 hour. A sample was then withdrawn and analyzed by infrared spectoscopy. A strong band located at 1700 centimeters$^{-1}$, which was characteristic of esters, indicates the phase transfer reagent allowed the reaction to proceed at a desirable rate.

EXAMPLE 4

A 150 ml flask was charged with potassium acetate (4.61 grams, 0.047 moles), phenylmethylvinylchlorosilane (8.46 grams, 0.046 moles), approximately 100 ml dry, oxygen free hexane and 0.02 grams 18-crown-6. The reaction was stirred 24 hours under an atmosphere of argon. A sample was analyzed by infrared spectroscopy and showed the presence of a single strong carbonyl absorption band at 1725 cm$^{-1}$. A proton nuclear magnetic resonance (NMR) spectrum showed the presence of the acetate methyl group.

EXAMPLE 5

A 150 ml flask was charged with sodium benzoate (7.21 grams, 0.050 moles), phenethyldimethylchlorosilane (9.67 grams, 0.049 moles), approximately 100 ml dry, oxygen free hexane and 0.01 grams tetra-n-butyl ammonium bromide. The reaction was stirred 24 hours at room temperature (22° C.) under an atmosphere of argon, producing a solid slurried in the reaction mixture. The solid was filtered off and the solvent was removed by evaporation, leaving a colorless liquid. The remaining liquid proved to be the corresponding silyl ester by proton NMR and infrared spectroscopy (carbonyl band at 1700 cm$^{-1}$). The isolated yield was 12.48 grams or 90% based on starting chlorosilane.

EXAMPLE 6

A 1000 ml flask was charged with sodium benzoate (35.00 grams, 0.249 moles), t-butyldimethylchlorosilane (31.08 grams, 0.2062 moles), approximately 700 ml dry, oxygen free hexane and 0.03 grams of 18-crown-6. The reaction was stirred under argon at room temperature (approximately 22° C.) for 22 hours, producing a solid slurried in the reaction mixture. The solid was filtered off to give a water white solution. The solvent was evaporated off leaving a colorless liquid. The remaining liquid proved to be the corresponding silyl ester by proton NMR and the presence of an infrared absorption at 1705 cm$^{-1}$. The yield was 45.18 grams of 93% based on starting chlorosilane.

EXAMPLE 7

A 50 ml flask is charged with magnesium benzoate (3.20 grams, 0.01201 moles), t-butyldimethylchlorosilane (1.79 grams, 0.0119 moles), approximately 30 ml dry, oxygen free hexane and 0.01 grams of tridecymethylammonium chloride. The reaction is allowed to stir under an atmosphere of argon at room temperature (22° C.) for 20 hours to produce a solid slurried in the reaction mixture. The solid is filtered. A colorless solution containing product and solvent is collected and the solvent evaporated. The remaining liquid, when analyzed by NMR, shows the presence of aromatic resonance, and infrared spectroscopy shows a carbonyl absorption near 1700 cm$^{-1}$.

EXAMPLE 8

A 100 ml flask is charged with (CH$_3$CO$_2$)$_3$Al (2.50 grams, 0.0171 moles), phenethyldimethylchlorosilane (3.36 grams, 0.0169 moles), approximately 75 ml dry, oxygen free hexane and 0.01 grams dioctadecyldimethylammonium chloride. The reaction is allowed to stir at room temperature for 24 hours under an atmosphere of argon to produce a solid slurried in the reaction mixture. The reaction mixture is filtered and the solvent is removed from the filtrate by evaporation to yield a colorless liquid product. The product is identified by NMR and infrared spectroscopy.

While certain embodiments and details have been shown for the purpose of illustrating this invention, it will be apparent to those skilled in this art that various changes and modifications may be made herein without departing from the spirit or scope of the invention.

We claim:

1. A method for the production of silyl esters of carboxylic acids, said ester having the general formula

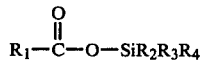

comprising reacting a carboxylic acid salt with a silicon halide in the presence of phase transfer catalysts selected from the group consisting of quaternary ammonium salts, crown ethers, and cryptates, wherein R$_1$, R$_2$, R$_3$ and R$_4$ are, independently, hydrogen, alkyl groups containing from 1 to 30 carbon atoms, cycloalkyl groups, aralkyl groups, alkaryl groups, aryl groups, and bicycloalkyl groups, all containing from 6 to 30 carbon atoms.

2. A method as described in claim 1 wherein the reaction takes place at a temperature of from about 10° C. to about 150° C.

3. A method as described in claim 2 wherein the silicon halide is a material having the general formula R$_2$, R$_3$ and R$_4$ SiX, wherein R$_2$ R$_3$ R$_4$ SiX are, independently, hydrogen, alkyl groups containing from 1 to 30 carbon atoms; cycloalkyl groups, aralkyl groups, alkaryl groups, aryl groups, bicycloalkyl groups each containing from 6 to 30 carbon atoms; halogen; O—SiR$_3$; —OR; —NR$_2$; and X is F, Cl, Br or I, and wherein when any of R$_2$, R$_3$ or R$_4$ are halogen, said halogen is no more reactive than the X designated halogen.

4. A method as described in claim 3 wherein the reaction is carried out in an inert solvent selected from the group consisting of alkanes such as hexanes, heptanes, isooctane, aromatics such as benzene, toluene, low polynuclear aromatic solvents, raffinate solvents and mixtures of these.

5. A method as described in claim 4 wherein the phase transfer catalyst is a quaternary ammonium salt selected from the group consisting of hexadecyltrihexylammonium bromide; trioctylethylammonium bromide; tridecylmethylammonium chloride; didodecyldimethylammonium chloride; tetraheptylammonium iodide; dioctadecyldimethylammonium chloride; tridecylbenzylammonium chloride; ditricosylmethylammonium chloride; tricaprylyldodecylammonium p-toluene sulfonate; tetranonylammonium hydroxide, N,N,N,N-tetramethyl-N,N-ditetradecyl-p-xylene-α,α'-diammonia dichloride; N,N,N'N'-tetramethyl-N,N'-dioctadecyl-x-dodecyl-y-xyleneα,α'diammonium dichloride; N,N-dioctadecyl-N-methylN-(sodiocarboxylmethyl)-ammonium chloride; N,N,N'-N-tetramethylN,N'-dioctadecyl-p-xyleneα,α'-diammonium dichloride; N,N,N',N-tetramethyl-N,N'dioctadecyl-1,2-ethyl'diammonium dibromide; N,N'-dimethyl-N,N,N'-N'-tetraheptadecyl-2-butene-1,4-diammonium chloride or mixtures of these.

6. A method as described in claim 4 wherein the phase transfer catalyst is a crown ether selected from the group consisting of 15-crown-5; 18-crown-6; dibenzo-18-crown-6 dicyclohexyl-18-crown-6; benzo-15-crown-5; alkyl-18-crown-6; alkyl-2,2,2-cryptate; benzo-2,2,2-cryptate; 2,2,2-cryptate 2,2,1-cryptate; dibenzo-24-crown-6; 12-crown-4 and mixtures of these.

7. A method as described in claim 4 wherein the carboxylic acid salt has the general formula

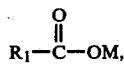

wherein M is selected from the group consisting of lithium, sodium, potassium, rubidium, cesium and mixtures of these.

8. A method as described in claim 4 wherein the carboxylic acid salt has the general formula

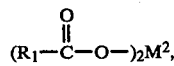

wherein $M^2$ is selected from the group consisting of magnesium, calcium, strontium, barium zinc, and mixtures of these.

9. A method as described in claim 4 wherein the carboxylic acid salt has the general formula

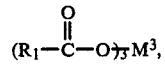

wherein $M^3$ is selected from the group consisting of aluminum, titanium, vanadium, iron, chromium and mixtures of these.

* * * * *